US008216986B2

(12) United States Patent  (10) Patent No.: US 8,216,986 B2
Parekh et al.  (45) Date of Patent: *Jul. 10, 2012

(54) LOW-PHOSPHOROUS LUBRICANT ADDITIVE

(76) Inventors: Kajal Parekh, Arlington, TX (US); Pranesh B. Aswath, Grapevine, TX (US); Harold Shaub, Irving, TX (US); Ronald L. Elsenbaumer, Arlington, TX (US)

( * ) Notice: Subject to any disclaimer, the term of this patent is extended or adjusted under 35 U.S.C. 154(b) by 941 days.

This patent is subject to a terminal disclaimer.

(21) Appl. No.: 11/182,023

(22) Filed: Jul. 14, 2005

(65) Prior Publication Data

US 2006/0014652 A1  Jan. 19, 2006

Related U.S. Application Data

(63) Continuation-in-part of application No. 10/965,686, filed on Oct. 14, 2004, now Pat. No. 7,074,745.

(60) Provisional application No. 60/511,290, filed on Oct. 15, 2003.

(51) Int. Cl.
- *C10M 137/10* (2006.01)
- *C07F 15/02* (2006.01)
- *C07F 9/02* (2006.01)
- *C07F 9/165* (2006.01)

(52) U.S. Cl. ........ 508/368; 508/165; 508/171; 508/371; 508/433; 556/13; 556/24; 556/25

(58) Field of Classification Search .................. 508/368, 508/369, 371; 556/13, 14, 24, 25
See application file for complete search history.

(56) References Cited

U.S. PATENT DOCUMENTS

| | | | |
|---|---|---|---|
| 2,884,431 A | 4/1959 | Smith et al. | |
| 2,959,544 A | 11/1960 | Smith et al. | |
| 3,662,034 A * | 5/1972 | Oswald et al. | 558/213 |
| 4,130,492 A | 12/1978 | Longo | |
| 4,313,761 A * | 2/1982 | Joyce et al. | 106/18.19 |
| 4,824,690 A | 4/1989 | Heinecke et al. | |
| 4,832,859 A | 5/1989 | Basset et al. | |
| 5,133,886 A | 7/1992 | Hata | |
| 5,242,506 A | 9/1993 | Barber et al. | |
| 5,385,683 A | 1/1995 | Ransom | |
| 5,595,962 A | 1/1997 | Caporiccio et al. | |

(Continued)

FOREIGN PATENT DOCUMENTS

GB  804777  11/1958

OTHER PUBLICATIONS

International Search Report & Written Opinion issued for PCT/US2006/034714 dated Mar. 30, 2007.

(Continued)

*Primary Examiner* — Walter D Griffin
*Assistant Examiner* — Vishal Vasisth
(74) *Attorney, Agent, or Firm* — Parks IP Law LLC; Collen A. Beard, Esq.

(57) ABSTRACT

A lubricant additive produced by the process comprising mixing a metal halide with an organophosphate, the metal halide participating as a reactant and reacting the metal halide and the organophosphate to produce a reaction mixture comprising the lubricant additive. Also disclosed is a lubricant produced by the process comprising forming a lubricant additive by reacting metal halide and organophosphate together to form a reaction mixture, the metal halide participating as a reactant, and adding at least a portion of the reaction mixture to a lubricant base.

32 Claims, 11 Drawing Sheets

| STRUCTURE NUMBER | POSSIBLE STRUCTURES | THEORETICAL PEAKS IN $^{31}$P NMR (ppm) | REFERENCES |
|---|---|---|---|
| 1 | [(RO)$_2$P(S)S]$_2$Zn NEUTRAL ZDDP (SECONDARY) | 94, 102-93, 95.8 | 1,5 |
| 2 | (RS)$_3$P(S), R>CH$_3$ | 92.9, 90-98 | 4,2 |
| 3 | (RO)(R'S)P(O)SZn$^-$ | 68-90 | 2 |
| 4 | (RO)$_2$(RS)PS, R>CH$_3$ | 92-96, 94.9, 85-93 | 2,4,1 |
| 5 | BASIC ZDDP | 102-110, 100(SEC) | 1 |
| 6 | >P(S)SZn$^-$ | 99-104 | 2 |
| 7 | (RO)$_2$P(S)(SR) | 100 | 3 |
| | [(RO)$_2$P(S)S]$_2$Zn NEUTRAL ZDDP (PRIMARY) | 104 | 3 |
| 8 | R(R'S)$_2$PS, R=CH$_3$, R'>CH$_3$ | -74 +-3.0 | 4 |
| 9 | (RO)$_3$PS, R=CH$_3$, R = ANY ALKYL | -73, 50-82 | 4,2 |
| 10 | MeP(S)Cl$_2$ | -79.8 | 4 |
| 11 | (RO)$_2$(S)PSP(S)(OR)$_2$ | 76-83, 78.4-83.4 | 2,5 |
| 12 | >P(S)(SH) | 78-83 | 2 |
| | (RO)(R'S)P(O)SZn$^-$ | 68-90 | 2 |
| 13 | SPH(OCH$_3$)$_2$ | 74 | 5 |

U.S. PATENT DOCUMENTS

| | | |
|---|---|---|
| 5,641,731 A | 6/1997 | Baumgart et al. |
| 5,767,045 A | 6/1998 | Ryan |
| 5,877,128 A | 3/1999 | Greer |
| 6,045,692 A | 4/2000 | Bilski et al. |
| 6,152,978 A | 11/2000 | Lundquist |
| 6,361,678 B1 | 3/2002 | Childs et al. |
| 6,413,918 B1 | 7/2002 | Beatty et al. |
| 6,541,430 B1 | 4/2003 | Beatty |
| 6,642,186 B2 | 11/2003 | Beatty et al. |
| 6,734,320 B2 | 5/2004 | Beatty et al. |
| 6,764,984 B2 | 7/2004 | Beatty |
| 6,835,218 B1 | 12/2004 | Drozd et al. |
| 2001/0038048 A1 | 11/2001 | Blanton et al. |
| 2005/0119135 A1 | 6/2005 | Shaub et al. |
| 2006/0040832 A1 | 2/2006 | Zhang et al. |
| 2006/0063683 A1 | 3/2006 | Parekh et al. |

OTHER PUBLICATIONS

International Search Report and Written Opinion issued for PCT/US04/34272 dated Sep. 1, 2005.

International Search Report and the Written Opinion issued for PCT/US2007/00781, dated Sep. 26, 2007; 8 pages.

International Search Report and the Written Opinion issued for PCT/US2007/69633; dated Oct. 31, 2007; 8 pages.

\* cited by examiner

FIG. 1

| STRUCTURE NUMBER | POSSIBLE STRUCTURES | THEORETICAL PEAKS IN $^{31}$P NMR (ppm) | REFERENCES |
|---|---|---|---|
| 1 | [(RO)$_2$P(S)S]$_2$Zn NEUTRAL ZDDP (SECONDARY) | 94, 102-93, 95.8 | 1,5 |
| 2 | (RS)$_3$P(S), R>CH$_3$ | 92.9, 90-98 | 4,2 |
| 3 | (RO)(R'S)P(O)SZn$^-$ | 68-90 | 2 |
| 4 | (RO)$_2$(RS)PS, R>CH$_3$ | 92-98, 94.9, 85-93 | 2,4,1 |
| 5 | BASIC ZDDP | 102-110, 100(SEC) | 1 |
| 6 | >P(S)SZn$^-$ | 99-104 | 2 |
| 7 | (RO)$_2$P(S)(SR) | 100 | 3 |
|  | [(RO)$_2$P(S)S]$_2$Zn NEUTRAL ZDDP (PRIMARY) | 104 | 3 |
| 8 | R(R'S)$_2$PS, R=CH$_3$, R'>CH$_3$ | -7.4 + -3.0 | 4 |
| 9 | (RO)$_3$PS, R=CH$_3$, R = ANY ALKYL | -7.3, 50-82 | 4,2 |
| 10 | MeP(S)Cl$_2$ | -79.8 | 4 |
| 11 | (RO)$_2$(S)PSP(S)(OR)$_2$ | 76-83, 78.4-83.4 | 2,5 |
| 12 | >P(S)(SH) | 78-83 | 2 |
|  | (RO)(R'S)P(O)SZn$^-$ | 68-90 | 2 |
| 13 | SPH(OCH$_3$)$_2$ | 74 | 5 |

| STRUCTURE NUMBER | ELEMENTS | ZDDP UNTREATED (ppm) | ZDDP TREATED 20 MINUTES/ 150c/NITROGEN (ppm) | ZDDP-FeF$_3$ TREATED 'SUPERNATANT ONLY' 20 MINUTES/ 150c/NITROGEN (ppm) |
|---|---|---|---|---|
| 1 | PHOSPHORUS | 1057 | 1000 | 1000 |
| 2 | SULFUR | 1261 | 1365 | 1267 |
| 3 | ZINC | 1150 | 1148 | 1203 |
| 4 | IRON | 0 | 0 | 1-2 |
| 5 | FLUORINE | 0 | 0 | 163 |

$\delta p = 65.5$ $\delta p = 68.4$ $\delta p = 31.7$

X = R, OR, SR, R MAY BE SAME OF DIFFERENT
x >= 1
n ~ 1 OR 2

X = R, OR, SR
(COMBINATION OF ANY GROUPS AT ANY TIME)
R MAY BE SAME OR DIFFERENT AT THE SAME TIME
AT LEAST ONE O OR S IN THE STRUCTURE AT ANY TIME

+

ANY ONE STRUCTURE FROM
8(A,B,C) FOR MIDDLE BAND

LOW-PHOSPHOROUS LUBRICANT ADDITIVE

CROSS-REFERENCE TO RELATED APPLICATIONS

This application claims priority to U.S. provisional application Ser. No. 60/511,290 filed on Oct. 15, 2003, entitled "ENGINE OIL ADDITIVE," and U.S. patent application Ser. No. 10/965,686 now U.S. Pat. No. 7,074,745, filed Oct. 14, 2004, entitled "ENGINE OIL ADDITIVE."

TECHNICAL FIELD

The present application relates generally to lubricant additives and, more particularly, to alternative lubricant additives that reduce the quantity of zinc dialkyldithiophosphate (ZDDP) and phosphorous in lubricants.

BACKGROUND OF THE INVENTION

Lubricants comprise a variety of compounds selected for desirable characteristics such as anti-wear and anti-friction properties. Many of these compounds are used in enormous quantities. For example, more than four billion quarts of crankcase oil are used in the United States per year. However, many compounds currently in use also have undesirable characteristics. Currently available crankcase oils generally include the anti-wear additive zinc dialkyldithiophosphate (ZDDP), which contains phosphorous and sulfur. Phosphorous and sulfur poison catalytic converters causing increased automotive emissions. It is expected that the EPA eventually will mandate the total elimination of ZDDP or will allow only extremely low levels of ZDDP in crankcase oil. However, no acceptable anti-wear additives to replace ZDDP in engine oils are currently available.

It is an object of the present invention to provide an environmentally friendly anti-wear additive for lubricants, wherein the amounts of phosphorous and sulfur in the anti-wear additive are significantly reduced and approach zero. It is another object of the present invention to produce compounds with desirable anti-wear and anti-friction characteristics.

BRIEF SUMMARY OF THE INVENTION

Embodiments of the invention comprise methods for preparing lubricant additives by reacting at least one organophosphate compound and at least one metal halide where the at least one metal halide participates in the reaction primarily as a reactant. Organophosphates used in embodiments of the invention may comprise metal organophosphates, organothiophosphates, metal organothiophosphates, and other compounds comprising organophosphate groups. The organophosphate used in a preferred embodiment is a metal organophosphate, such as ZDDP. In other embodiments, one of the organophosphate compounds used is ZDDP mixed with smaller molecular weight organophosphates. In one embodiment, the at least one organophosphate and at least one metal halide are reacted together at about −20° C. to about 150° C. In a preferred embodiment, the reactant mixture is heated to a temperature of about 60° C. to about 150° C. The reaction is allowed to continue from about 20 minutes to about 24 hours. Both supernatants and precipitates formed during the reaction may be used as lubricant additives in certain embodiments of the present invention. These lubricant additives may be added to lubricants such as oils, greases, etc. Automatic transmission fluids, crankcase fluids, engine oils, hydraulic oils, and gear oils.

Other embodiments of the present invention react a mixture of powdered, masticated metal halide with an organophosphate or an organophosphate mixture to form a lubricant additive. The metal halide used is metal fluoride in a preferred embodiment of the invention. In a preferred embodiment, the metal fluoride and the organophosphate are reacted together at about −20° C. to about 150° C. to form a lubricant additive. The lubricant additive is then added to a lubricant. The lubricants to which the lubricant additive is added are preferably fully formulated GF4 engine oils without ZDDP. However, other lubricants may be used such as those listed above.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIG. 1 is a table showing representative organophosphate compounds that may be used with embodiments of the present invention;

DETAILED DESCRIPTION OF THE INVENTION

Embodiments of the present invention provide improved lubricant additives. Lubricant additives according to embodiments of the present invention may be added to lubricants such as greases, crankcase oils, hydrocarbon solvents, etc. In a preferred embodiment of the present invention, lubricant additives are mixed with a fully formulated engine oil without ZDDP. The term "fully formulated oil" as used here to illustrate certain embodiments of the present invention are engine oils that include additives, but not zinc dialkyldithiophosphate (ZDDP). In certain embodiments, the fully formulated oil may be, for example, a GF4 oil with an additive package comprising standard additives, such as dispersants, detergents, and anti-oxidants, but without ZDDP.

Certain embodiments of the present invention comprise methods for preparing lubricant additives by reacting together one or more organophosphates such as metal organophosphates like ZDDP and one or more metal halides such as ferric fluoride, where the metal halide participates in the reaction primarily as a reactant. Metal halides used with embodiments of the present invention may be, for example, aluminum trifluoride, zirconium tetrafluoride, titanium trifluoride, titanium tetrafluoride, and combinations thereof. In other embodiments, other transition metal halides are used, such as, for example, chromium difluoride and trifluoride, manganese difluoride and trifluoride, nickel difluoride, stannous difluoride and tetrafluoride, and combinations thereof. Ferric fluoride is used in preferred embodiments of the present invention. Ferric fluoride may be produced according to a process described in co-pending U.S. patent application Ser. No. 10/662,992 filed Sep. 15, 2003, the contents of which are herein incorporated by reference.

Figure 2A:
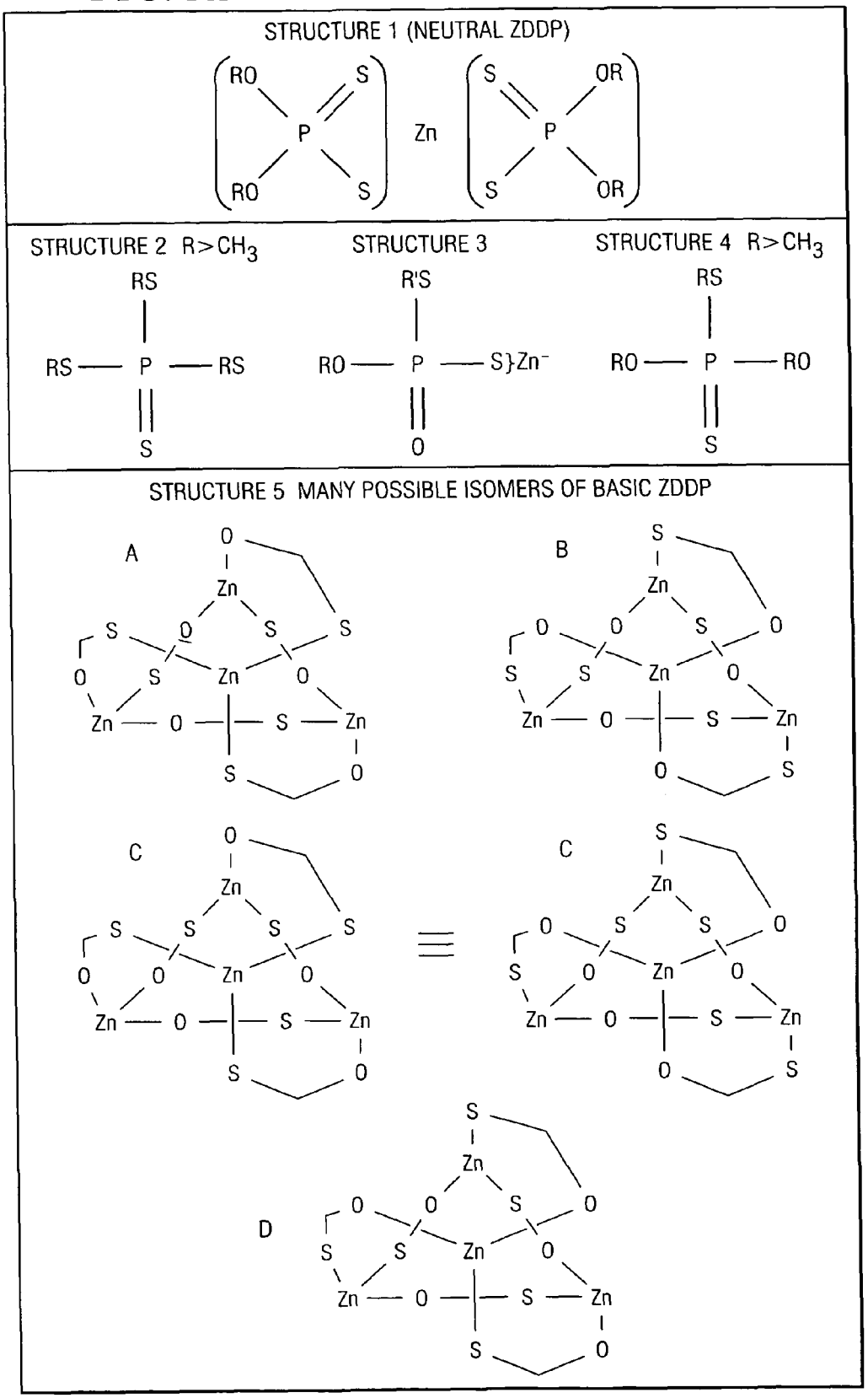
FIGS. 2A-2C show structures associated with some of the organophosphates that may be used with embodiments of the present invention.
Figure 2B:
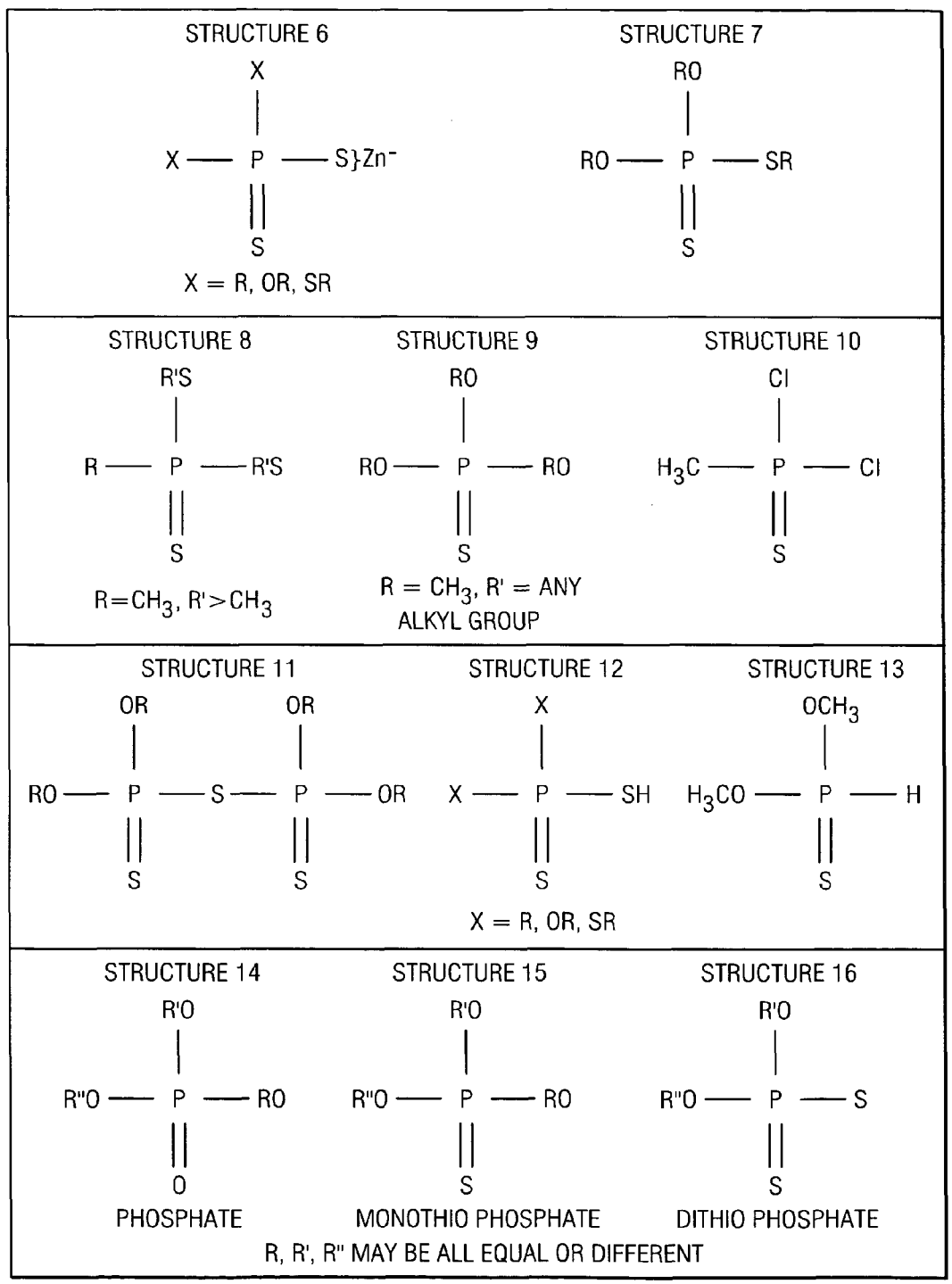
Figures 2C, 3:
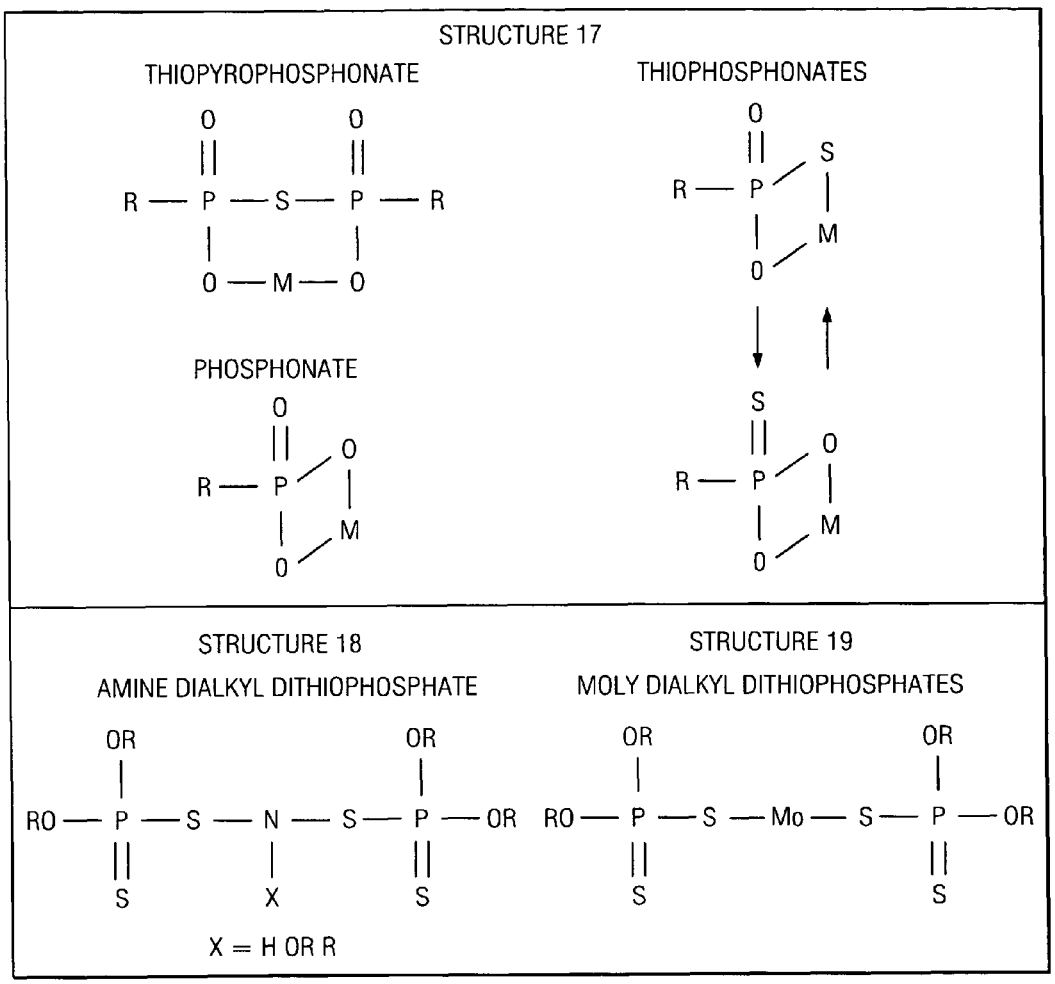
FIG. 3 is a table presenting experimental results showing the presence of fluorine in reaction supernatants.

FIG. 1 is a table showing several of the organophosphate compounds that may be used with embodiments of the present invention. Generally, dithiophosphates and amine and amine salts of monothiophosphates and dithiophosphates may be used. Other organophosphates listed in FIG. 1 include neutral ZDDP (primary), neutral ZDDP (secondary), basic ZDDP, $(RS)_3P(s)$ where $R>CH_3$, $(RO)(R'S)P(O)SZn^-$, $(RO)_2(RS)PS$ where $R>CH_3$, $P(S)(S)Zn^-$, $(RO)_2P(S)(SR)$, $R(R'S)_2PS$ where $R=CH_3$ and $R'>CH_3$, $(RO)_3PS$ where $R=CH_3$ and $R'=$alkyl, $MeP(S)Cl_2$, $(RO)_2(S)PSP(S)(OR)_2$, $P(S)(SH)$, $(RO)(R'S)P(O)SZn^-$, $SPH(OCH_3)_2$, where $R=$any alkyl and $R'=$any alkyl, and combinations thereof. The chemical structures of representative compounds from FIG. 1 and additional organophosphate compounds that may be used with the invention are shown in FIGS. 2a-2c. In certain embodiments of the present invention, organophosphates not shown in FIGS. 1 and 2a-2c may be used. The organophosphate ZDDP is used in preferred embodiments of the present invention. Embodiments using ZDDP, alone or in combination with other organophosphates, can use ZDDP in one or more moieties. Preferably, the ZDDP used is the neutral or basic moiety. Some of the ZDDP moieties are shown in FIG. 2a as structures 1 and 5.

The organophosphate and metal halide are reacted together at about −20° C. to about 150° C. In a preferred embodiment, the reactant mixture is heated to a temperature of about 60° C. to about 150° C. The reaction is allowed to continue from about 20 minutes to about 24 hours. Generally, as temperature is decreased in embodiments of the invention, the duration of the reaction is increased. Various additional reaction parameters may be used, such as performing the reaction under certain gases such as nitrogen or noble gases, or stirring the reactants to encourage reaction progress. In certain embodiments, the organophosphate and metal halide are reacted together in a lubricant base to form an improved lubricant. Both supernatants and precipitates formed during a reaction may be used as lubricant additives in certain embodiments of the present invention. Supernatants and precipitates may be separated using standard techniques such as filtration or centrifugation known to those skilled in the art. Precipitates remaining after reactions between organophosphates and metal halides may comprise metal-containing solid compounds such as iron alkyl ethers, fluorocarbons, organofluorophosphorous compounds, and/or organothiophosphates.

In one embodiment of the present invention, a lubricant additive is added to a commercial engine oil containing an additive package without ZDDP and with either 0 ppm or 80 ppm of a molybdenum-containing additive. In this embodiment, masticated ferric fluoride is prepared from powder by combining ferric fluoride with a suspending agent and a base oil. In certain embodiments of the invention, masticated ferric fluoride and ZDDP sufficient to provide 0.01 wt % phosphorous content, in the oil, are mixed together and heated at 60° C. for one hour to produce a reaction mixture. In other embodiments, different heating times and/or temperatures are used. The reaction mixture supernatant is then separated from precipitate solids to produce a lubricant additive. This lubricant additive is then added to engine oil that does not include ZDDP. The resultant improved engine oil is then used in an appropriate application such as, for example, an engine crankcase. Improved engine oil produced according to an embodiment of the present invention are used in engines found in, for example, automobiles, trucks, motorcycles, generators, lawn equipment, etc.

FIG. 3 is a table presenting experimental results showing that fluorine, presumably donated by the metal halide ferric fluoride, remains in a reaction supernatant formed using an embodiment of the present invention. In this experiment, samples of untreated ZDDP, untreated ZDDP under an inert atmosphere, and ZDDP reacted with ferric fluoride under an inert atmosphere were chemically analyzed. The ASTM D3120 protocol was used for sulfur and ASTM D5185 for phosphorous, zinc, and iron. Fluorine analysis was conducted separately by completely combusting to a fluoride and using iron chromatography. The results of the analysis shown in FIG. 3 indicate that no fluorine was present in the supernatant samples from either the untreated ZDDP or the untreated ZDDP under inert atmosphere. However, significant quantities of fluorine (163 parts per million) were found in supernatant samples taken from the ZDDP reacted with ferric fluoride. Also, iron levels were extremely low (1-2 parts per million) in those samples, indicating that the fluorine present in the supernatant has bonded to an element other than iron.

Figure 4:
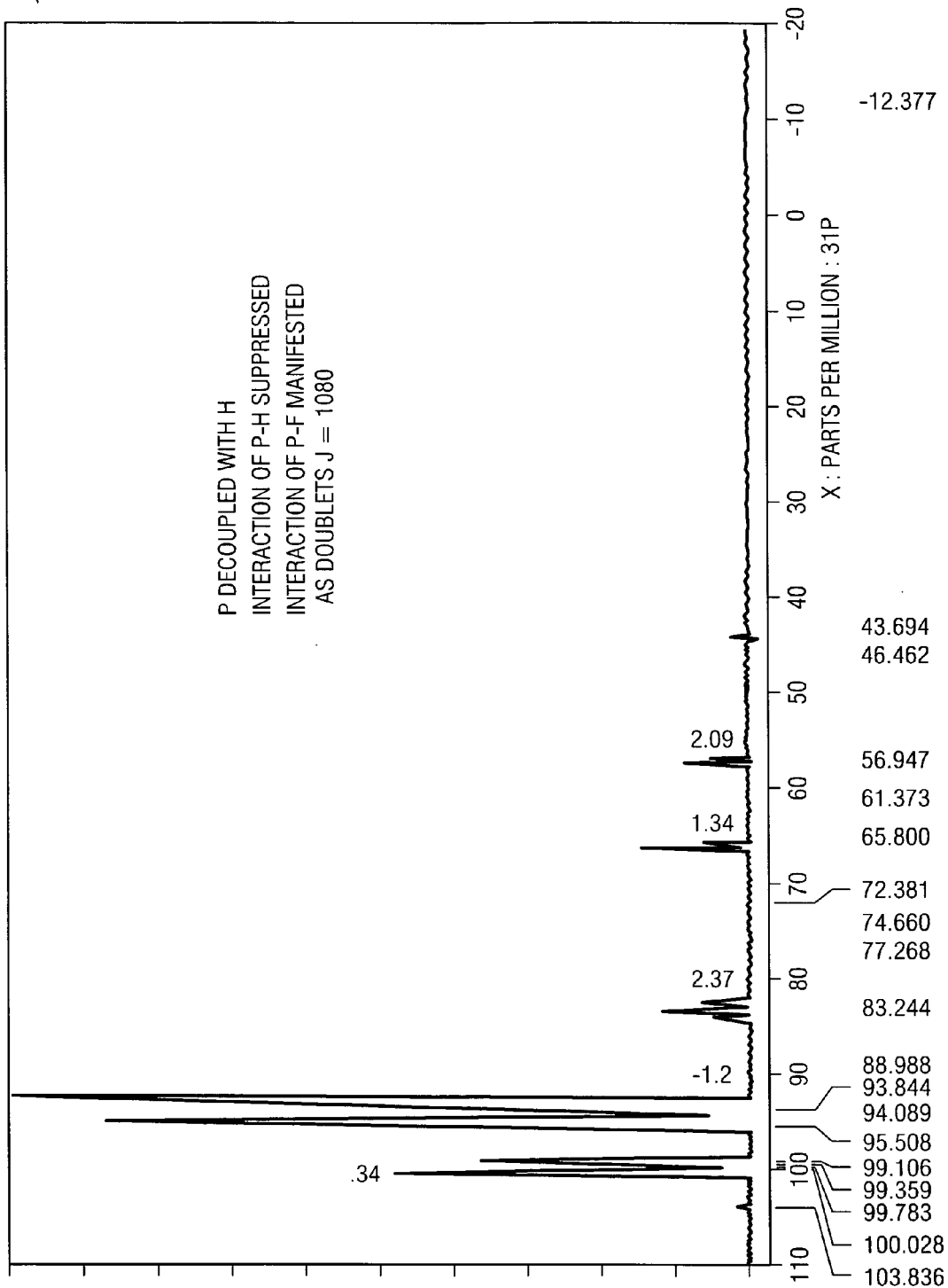
FIG. 4 shows a $^{31}P$ NMR spectra of supernatant from a reaction between ZDDP and ferric fluoride.

FIG. 4 shows a $^{31}P$ NMR spectrum of supernatant from a reaction between ZDDP and ferric fluoride. The spectra shows the presence of doublets resulting from the interaction of bound phosphorous and fluorine atoms in compounds present in the supernatant sample. The experiments summarized in FIGS. 3 and 4 illustrate that the metal halide participates primarily as a reactant in embodiments of the present invention.

Figure 5:
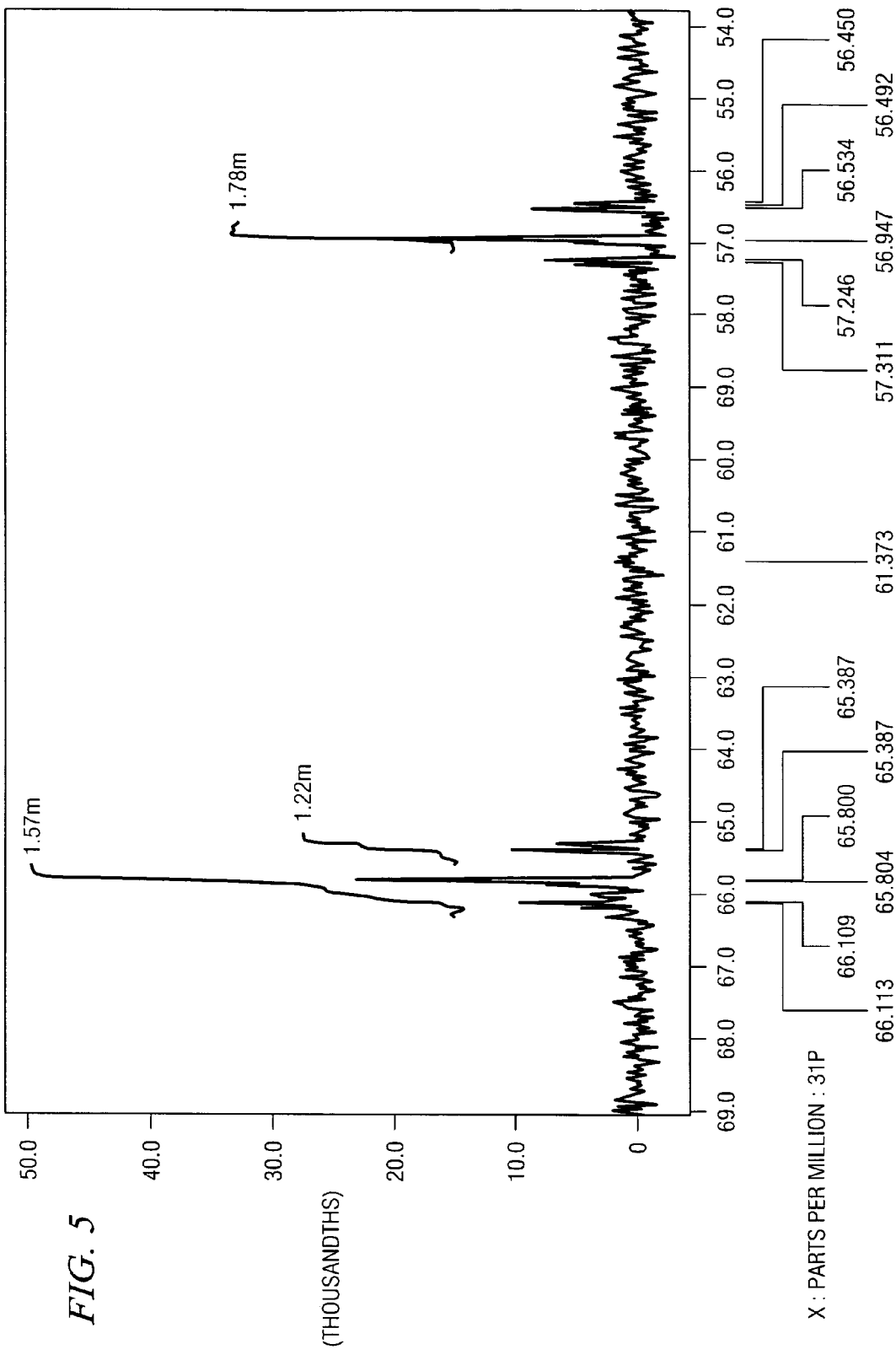
FIG. 5 is a $^{31}P$ NMR spectrum of supernatant from a reaction between ZDDP and ferric fluoride.

FIGS. 5-10 show experimental results and possible structures for reaction products formed by embodiments of the present invention. FIG. 5 is a $^{31}P$ NMR spectrum ($^{1}H$ decoupled to suppress phosphorous-hydrogen peaks) of supernatant from a reaction between ZDDP and ferric fluoride showing the formation of a fluoro-phosphorous compound. A doublet located at approximately 57 ppm and 66 ppm is due to a phosphorous-fluorine bond with J=1080. Each doublet peak is composed of multiple peaks that are apparent triplets.

Figure 6:
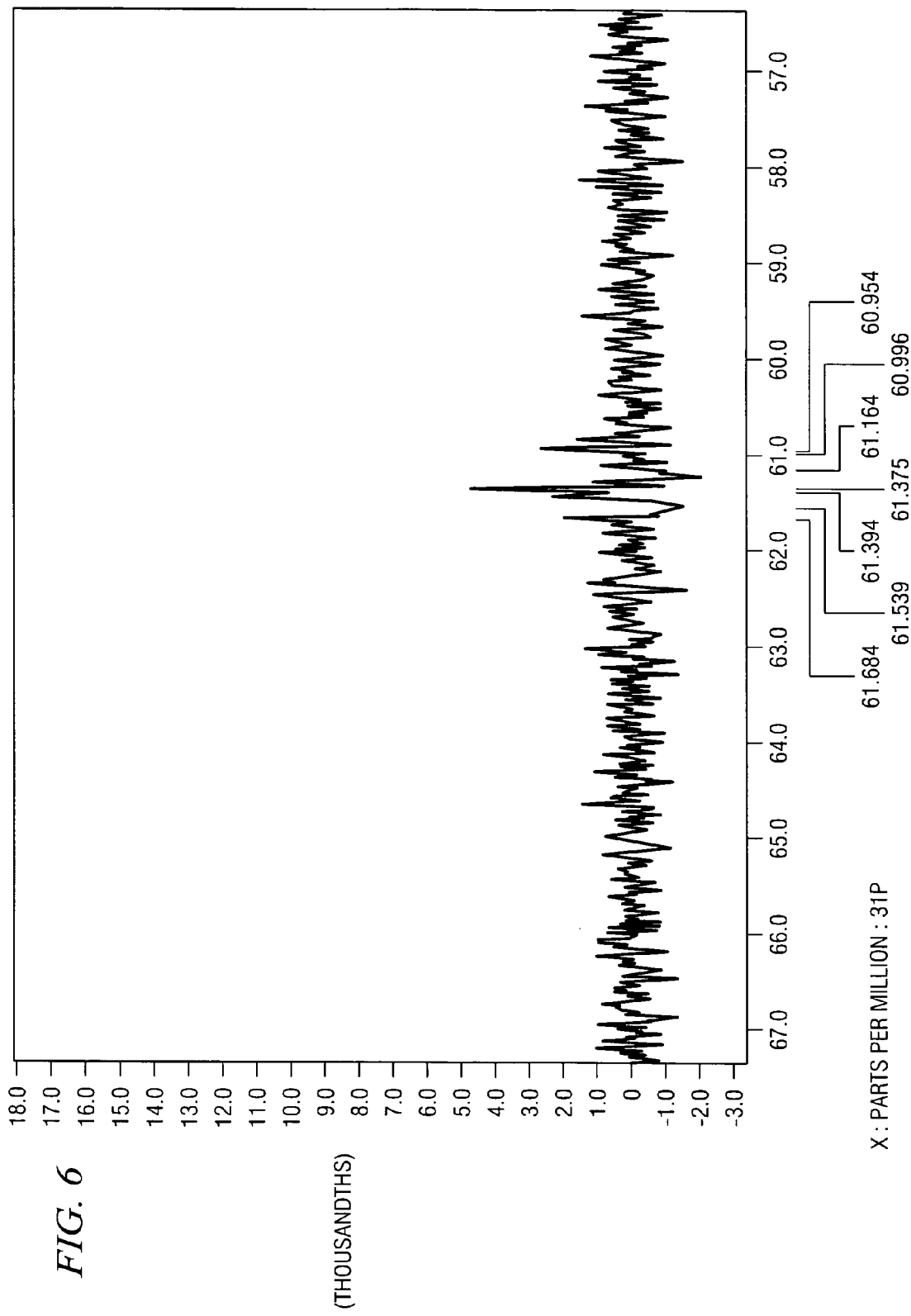
FIG. 6 is another $^{31}P$ NMR spectrum of supernatant from a reaction between ZDDP and ferric fluoride.
Figure 7A:
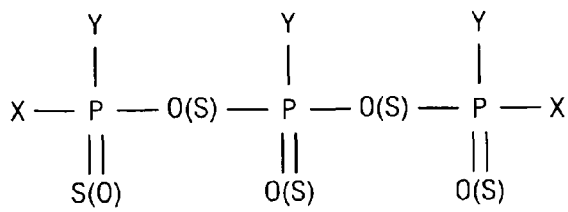
FIGS. 7-10 show organophosphate structures that may be used with embodiments of the present invention.
Figure 7B:
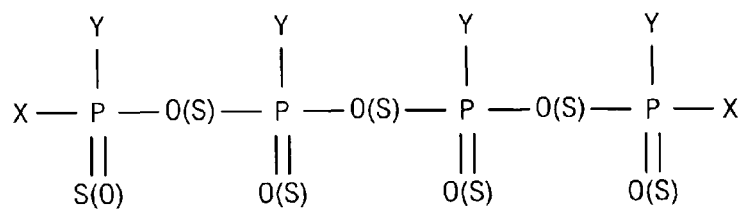
Figure 7C:
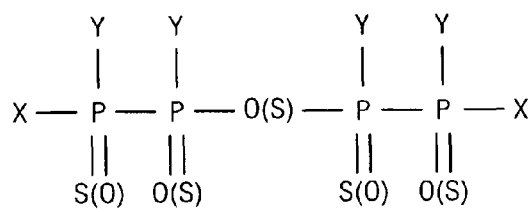
Figure 7D:
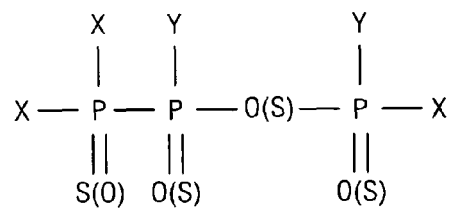
Figure 8A:
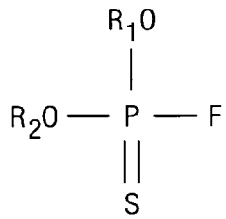
Figure 8B:
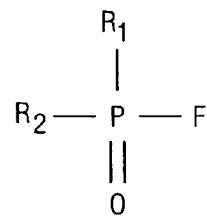
Figure 8C:
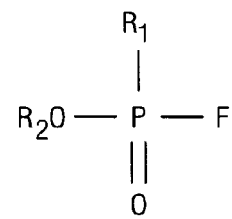
Figure 8D:
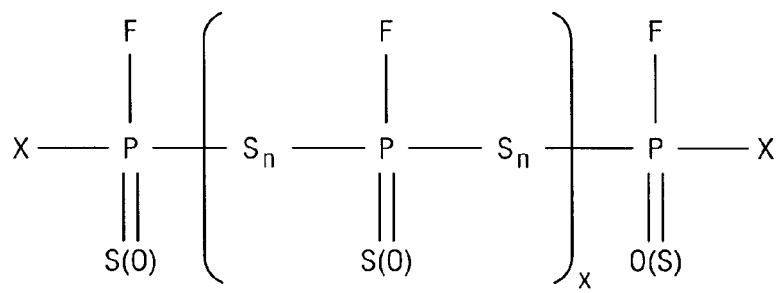
Figure 9:
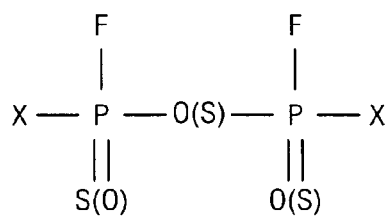

FIG. 6 is a $^{31}P$ NMR spectrum ($^{19}F$ decoupled to suppress phosphorous-fluorine peaks) of supernatant from a reaction between ZDDP and ferric fluoride. Comparison with FIG. 5 shows that the triplets present in FIG. 5 have merged to a single triplet at approximately 61 ppm located midway between the former triplet locations at approximately 57 ppm and 66 ppm. The merging of the two triplets indicates that the origin of the doublet in FIG. 5 was from a phosphorous-fluorine bond. Also, the fact that a triplet still remains in this spectrum indicates that the origin of the triplet is from a phosphorous-phosphorous backbone and not from a phosphorous-hydrogen or phosphorous-fluorine backbone.

The three peaks in the triplets of FIGS. 5 and 6 can be from spin-spin splits from at least 3 different interacting phosphorous atoms in the same structure. Chemical shifts of 3 phosphorous atoms are nearly the same, such that relative chemical shifts are less than or equal to coupling constants of the phosphorous, i.e. the origin of the shifts result from a second order spectra rather than a first order. Four possible compounds that can produce the NMR spectra of FIGS. 5 and 6 are shown in FIG. 7. In all structures shown in FIG. 7, X=R, OR, and/or SR. R refers to an alkyl group, and may be the same or different at the same time within the same structure. The O(S) refers to either an oxygen or sulfur atom being present at one time. Y equals F or another halogen. At least one Y equals F.

If the peaks in the triplets of FIGS. 5 and 6 are not arising from a phosphorous-phosphorous backbone, then chemical structures such as those shown in FIG. 8 may be responsible for the spectra. In the case of structures (a)-(c) shown in FIG. 8, the origin of the multiple peaks in the spectra may result from the different environment surrounding the phosphorous atoms. In compound (d) shown in FIG. 8, the separation of the phosphorous atoms is large enough to suppress any interaction between them and the origin of the multiple peaks in the spectra result from the different environment surrounding the phosphorous atoms. In all of the structures shown in FIG. 8, the presence of a phosphorous-fluorine bond is certain. In all of the FIG. 8 structures, R equals an alkyl group.

If two of the shoulder peaks in the NMR triplets shown in FIGS. 5 and 6 arise from spin-spin coupling of two phosphorous atoms on the backbone then the third dominant peak at the center may arise from any one of the compounds shown in FIG. 8. The shoulder peaks (smaller peaks within FIGS. 5 and 6) arise from the structure of the kind shown in FIG. 9. The dominant peak (the middle peak) can arise from any one of the three structures (a), (b), or (c) shown in FIG. 8.

Figure 10:
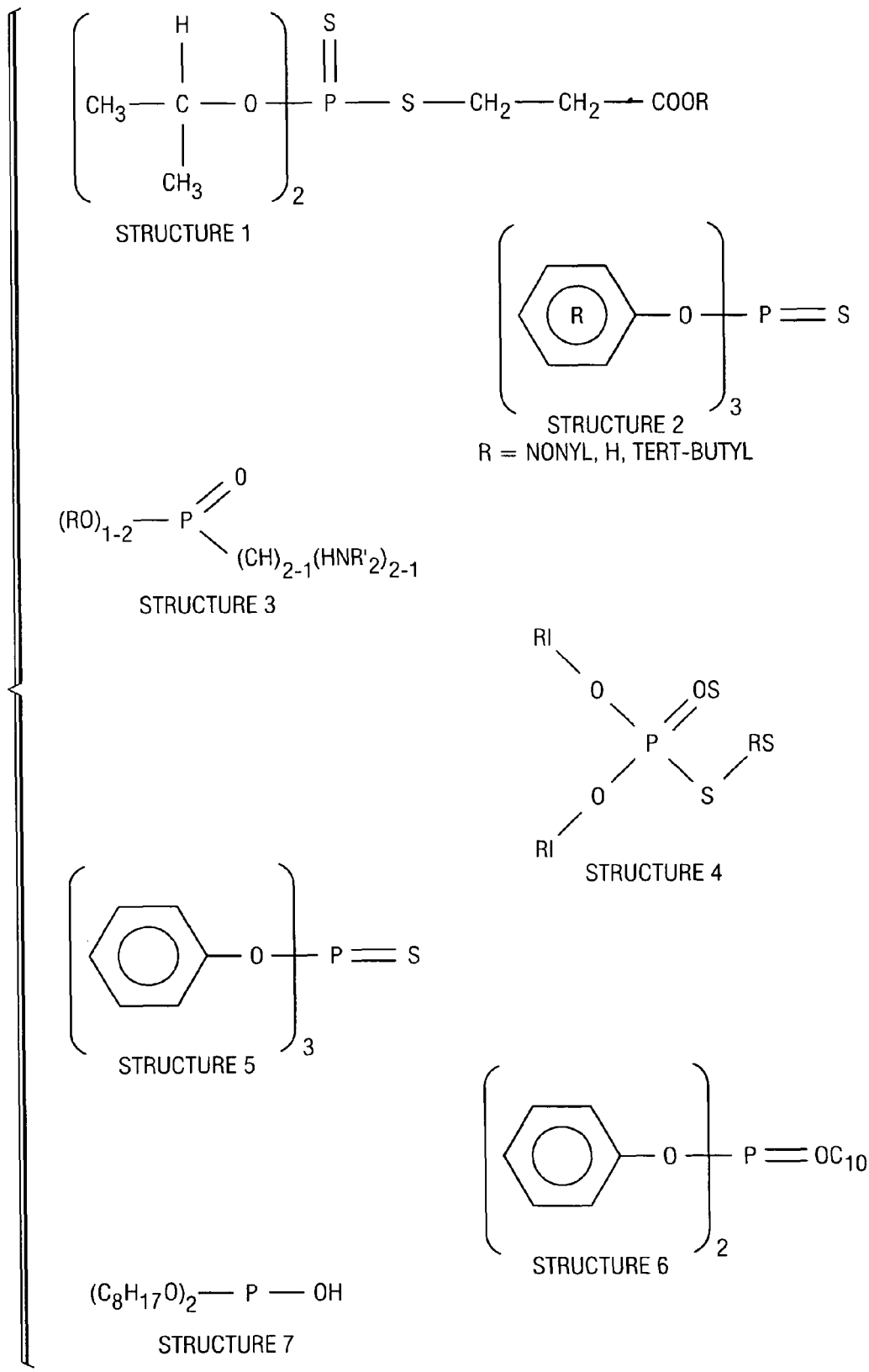

Additional organophosphate structures that may be usable with embodiments of the present invention are shown in FIG. 10. The organophosphate structures specifically disclosed herein are representative structures and are in no way intended to limit embodiments of the present invention to those structures. Many embodiments of the present invention utilize organophosphate compounds not specifically shown.

Experiments were performed to evaluate lubricant formulations comprising lubricant additives produced according to embodiments of the invention. Generally, wear volume comparisons were used to compare the lubricants and lubricant additives produced according to embodiments of the invention. The experiments were conducted on a modified Ball on Cylinder machine. The machine was modified to accept standard Timken Roller Tapered Bearings, where the outer surface of the cup was used for wear testing. In order to generate consistent results a protocol was established to prepare the surface prior to wear testing. The protocol comprises two phases: break in and the actual test.

The break in protocol begins with preparation of the ring and the ball by cleaning with hexane and acetone followed by brushing. Then 50 μL of break in oil comprising base oil plus ZDDP sufficient to provide 0.1 wt % phosphorous, in the oil, is applied to the center of the surface of the ring. For the first 500 cycles, a constant load of 6 kg is applied, then increased gradually to 15 kg for the next 1500 cycles at 700 rpm. The rotation is then stopped and the ring and the ball cleaned on the spot without removing them.

For the actual test, the lubricant being tested is applied to the center of the surface of the ring. As with break in, a constant load of 6 kg is applied for the first 500 cycles. For the next 1500 cycles, the load is gradually increased to 24 kg. The weight used for the protocol may vary in some tests. Up to 23000 additional cycles at 700 rpm may be used in certain variations of the protocol during which the load is applied constantly and data acquisition is performed.

Figure 11:
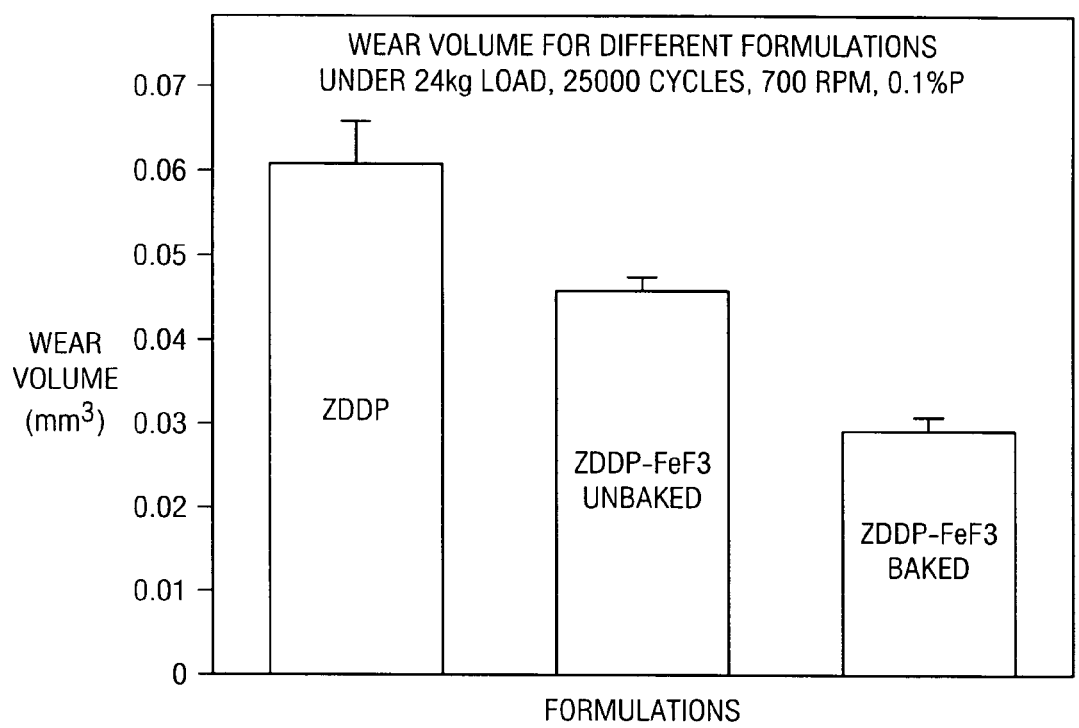
FIG. 11 shows a wear volume experiment comparing lubricant oils to which were added different lubricant additives.

FIG. 11 illustrates a profilometric wear volume result comparison of lubricant oils to which were added ZDDP alone, supernatant from ZDDP and ferric fluoride that were combined, but not heated, and supernatant from ZDDP and ferric fluoride that were combined and heated at 150° C. for 20 minutes. The data from the experiment shows that there is a greater than 50% reduction in wear volume when comparing the addition of ZDDP alone to the addition of supernatant produced by reacting ZDDP and ferric fluoride with heat. The experiment also shows that the reaction between ZDDP and ferric fluoride appears to progress at room temperature, as there was a significant reduction in wear volume when using the room temperature supernatant with a lubricant oil. The results show that the lubricant oil comprising lubricant additive produced according to an embodiment of the present invention is superior in minimizing the wear volume of a bearing used in the modified Ball on Cylinder test described above.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. The lubricant additive produced by the process comprising:
    mixing a metal fluoride with a pentavalent, mono- or di-thiophosphate, the metal fluoride participating as a reactant, wherein the metal fluoride is selected from the group consisting of: aluminum trifluoride, zirconium tetrafluoride, titanium trifluoride, titanium tetrafluoride, ferric fluoride, chromium difluoride, chromium trifluoride, nickel difluoride, stannous difluoride, stannous tetrafluoride, and combinations thereof; and
    reacting the metal fluoride and the pentavalent, mono- or di-thiophosphate to produce a reaction mixture comprising the lubricant additive, wherein said reacting comprises heating to a temperature from about 60° C. to about 125° C., the reaction producing, in the lubricant additive, at least one compound that comprises at least one phosphorus-fluorine bond.

2. The lubricant additive of claim 1 produced by the process further comprising:
    separating said reaction mixture into phases, at least one phase comprising said lubricant additive.

3. The lubricant additive of claim 1 wherein the pentavalent, mono- or di-thiophosphate is selected from the group consisting of:
    neutral ZDDP (primary), neutral ZDDP (secondary), basic ZDDP, ZDDP salt, $(RS)_3P(s)$ where $R>CH_3$, $(RO)(R'S)P(O)SZn^-$, $(RO)_2(RS)PS$ where $R>CH_3$, $P(S)(S)Zn^-$, $(RO)_2P(S)(SR)$, $R(R'S)_2PS$ where $R=CH_3$ and $R>CH_3$, $(RO)_3PS$ where $R=CH_3$ and $R'=$alkyl, $MeP(S)Cl_2$, $(RO)_2(S)PSP(S)(OR)_2$, $P(S)(SH)$, $(RO)(R'S)P(O)SZn^-$, $SPH(OCH_3)_2$, and combinations thereof.

4. The lubricant additive of claim 1 wherein the metal fluoride is 0.4 wt % powdered, masticated ferric fluoride.

5. The lubricant additive of claim 1 wherein the pentavalent, mono- or di-thiophosphate is ZDDP sufficient to provide a phosphorous content of about 0.01 wt % to about 0.05 wt % in a lubricant.

6. The lubricant additive of claim 1 wherein said reacting is of a duration from about 20 minutes to about 24 hours.

7. A method of manufacturing a lubricant additive comprising:
    mixing a metal fluoride with a pentavalent, mono- or di-thiophosphate;
    reacting the metal fluoride and the pentavalent, mono- or di-thiophosphate to produce a reaction mixture, the metal fluoride participating as a reactant, wherein the metal fluoride is selected from the group consisting of: aluminum trifluoride, zirconium tetrafluoride, titanium trifluoride, titanium tetrafluoride, ferric fluoride, chromium difluoride, chromium trifluoride, nickel difluoride, stannous difluoride, stannous tetrafluoride, and combinations thereof and wherein said reacting comprises heating a temperature from about 60° C. to about 125° C.; and
    separating said reaction mixture into solid and liquid phases, at least one phase comprising said lubricant additive, the reaction producing, in the lubricant additive, at least one compound that comprises at least one phosphorus-fluorine bond.

8. The method of claim 7 wherein said lubricant additive is in the solid phase.

9. The method of claim 7 wherein said lubricant additive is in the liquid phase.

10. The lubricant additive of claim 7 wherein the pentavalent, mono- or di-thiophosphate is selected from the group consisting of:
    neutral ZDDP (primary), neutral ZDDP (secondary), basic ZDDP, ZDDP salt, $(RS)_3P(s)$ where $R>CH_3$, $(RO)(R'S)P(O)SZn^-$, $(RO)_2(RS)PS$ where $R>CH_3$, $P(S)(S)Zn^-$, $(RO)_2P(S)(SR)$, $R(R'S)_2PS$ where $R=CH_3$ and $R>CH_3$, $(RO)_3PS$ where $R=CH_3$ and $R'=$alkyl, $MeP(S)Cl_2$, $(RO)_2(S)PSP(S)(OR)_2$, $P(S)(SH)$, $(RO)(R'S)P(O)SZn^-$, $SPH(OCH_3)_2$, and combinations thereof.

11. The method of claim 7 wherein said reacting comprises reacting from about 20 minutes to about 24 hours.

12. The method of claim 7 wherein the pentavalent, mono- or di-thiophosphate is ZDDP sufficient to provide a phosphorous content of about 0.01 wt % to about 0.05 wt % in a lubricant.

13. The method of claim 7 wherein the metal fluoride is 0.4 wt % powdered, masticated metal fluoride.

14. A lubricant produced by the process comprising:
    forming a lubricant additive by reacting metal fluoride and pentavalent, mono- or di-thiophosphate together to form a reaction mixture, the metal fluoride participating as a reactant, wherein the metal fluoride is selected from the group consisting of: aluminum trifluoride, zirconium tetrafluoride, titanium trifluoride, titanium tetrafluoride, ferric fluoride, chromium difluoride, chromium trifluoride, nickel difluoride, stannous difluoride, stannous tetrafluoride, and combinations thereof and wherein said reacting comprises heating to a temperature from about 60° C. to about 125° C.; and
    adding at least a portion of the reaction mixture to a lubricant base, the reaction producing, in the lubricant additive, at least one compound that comprises at least one phosphorus-fluorine bond.

15. The lubricant produced by the process of claim 14 wherein said reaction mixture comprises a supernatant, said supernatant separated from said reaction mixture to form said lubricant additive.

16. The lubricant produced by the process of claim 14 wherein said reaction mixture comprises a precipitate, said precipitate separated from said reaction mixture to form said lubricant additive.

17. The lubricant produced by the process of claim 14 wherein said lubricant base is selected from the group consisting of:
    GF4 engine oil without ZDDP, automatic transmission fluids, crankcase fluids, engine oils, hydraulic oils, gear oils, and combinations thereof.

18. The lubricant produced by the process of claim 14 wherein the pentavalent, mono- or di-thiophosphate is selected from the group consisting of:
    neutral ZDDP (primary), neutral ZDDP (secondary), basic ZDDP, ZDDP salt, $(RS)_3P(s)$ where $R>CH_3$, $(RO)(R'S)P(O)SZn^-$, $(RO)_2(RS)PS$ where $R>CH_3$, $P(S)(S)Zn^-$, $(RO)_2P(S)(SR)$, $R(R'S)_2PS$ where $R=CH_3$ and $R>CH_3$, $(RO)_3PS$ where $R=CH_3$ and $R'=$alkyl, $MeP(S)Cl_2$, $(RO)_2(S)PSP(S)(OR)_2$, $P(S)(SH)$, $(RO)(R'S)P(O)SZn^-$, $SPH(OCH_3)_2$, and combinations thereof.

19. The lubricant produced by the process of claim 14 wherein the lubricant additive is formed by heating the metal fluoride and the pentavalent, mono- or di-thiophosphate together from about 20 minutes to about 24 hours.

20. A method for producing a lubricant comprising:
    forming a lubricant additive in a reaction mixture by reacting metal fluoride and pentavalent, mono- or di-thiophosphate together to form the reaction mixture, the metal fluoride participating as a reactant, wherein the metal fluoride is selected from the group consisting of: aluminum trifluoride, zirconium tetrafluoride, titanium trifluoride, titanium tetrafluoride, ferric fluoride, chromium difluoride, chromium trifluoride, nickel difluoride, stannous difluoride, stannous tetrafluoride, and combinations thereof and wherein said reacting comprises heating to a temperature from about 60° C. to about 125° C.; and
    adding at least a portion of the reaction mixture to a lubricant base to form said lubricant, the reaction producing, in the lubricant additive, at least one compound that comprises at least one phosphorus-fluorine bond.

21. The method of claim 20 wherein said reaction mixture comprises a supernatant, the method further comprising:
    separating said supernatant from said reaction mixture and adding at least a portion of said supernatant to said lubricant base.

22. The method of claim 20 wherein said reaction mixture comprises a precipitate, the method further comprising:
    separating said precipitate from said reaction mixture and adding at least a portion of said precipitate to said lubricant base.

23. The method of claim 20 wherein the pentavalent, mono- or di-thiophosphate is selected from the group consisting of:

neutral ZDDP (primary), neutral ZDDP (secondary), basic ZDDP, ZDDP salt, $(RS)_3P(s)$ where $R>CH_3$, $(RO)(R'S)P(O)SZn^-$, $(RO)_2(RS)PS$ where $R>CH_3$, $P(S)(S)Zn^-$, $(RO)_2P(S)(SR)$, $R(R'S)_2PS$ where $R=CH_3$ and $R>CH_3$, $(RO)_3,PS$ where $R=CH_3$ and $R'=alkyl$, $MeP(S)Cl_2$, $(RO)_2(S)PSP(S)(OR)_2$, $P(S)(SH)$, $(RO)(R'S)P(O)SZn^-$, $SPH(OCH_3)_2$, and combinations thereof.

24. The method of claim 20 wherein said lubricant is selected from the group consisting of:
GF4 engine oil without ZDDP, automatic transmission fluids, crankcase fluids, engine oils, hydraulic oils, gear oils, and combinations thereof.

25. The method of claim 20 wherein the lubricant additive is formed by heating fluoride and the pentavalent, mono- or di-thiophosphate together from about 20 minutes to about 24 hours.

26. A lubricant produced by the process comprising:
adding metal fluoride and pentavalent, mono- or di-thiophosphate to a lubricant base; and
reacting said metal fluoride and said pentavalent, mono- or di-thiophosphate to form a lubricant, the metal fluoride participating as a reactant, wherein the metal fluoride is selected from the group consisting of: aluminum trifluoride, zirconium tetrafluoride, titanium trifluoride, titanium tetrafluoride, ferric fluoride, chromium difluoride, chromium trifluoride, nickel difluoride, stannus difluoride, stannous tetrafluoride, and combinations thereof and wherein said reacting comprises heating to a temperature from about 60° C. to about 125° C., the reaction producing at least one compound that comprises at least one phosphorus-fluorine bond.

27. The lubricant produced by the process of claim 26 wherein said reaction mixture comprises a supernatant, said supernatant separated from said reaction mixture to form said lubricant.

28. The lubricant produced by the process of claim 26 wherein said reaction mixture comprises a solid lubricant.

29. The lubricant produced by the process of claim 26 wherein said lubricant base is selected from the group consisting of:
GF4 engine oil without ZDDP, automatic transmission fluids, crankcase fluids, engine oils, hydraulic oils, gear oils, and combinations thereof.

30. The lubricant produced by the process of claim 26 wherein the pentavalent, mono- or di-thiophosphate is selected from the group consisting of:
neutral ZDDP (primary), neutral ZDDP (secondary), basic ZDDP, ZDDP salt, $(RS)_3P(s)$ where $R>CH_3$, $(RO)(R'S)P(O)SZn^-$, $(RO)_2(RS)PS$ where $R>CH_3$, $P(S)(S)Zn^-$, $(RO)_2P(S)(SR)$, $R(R'S)_2PS$ where $R=CH_3$ and $R>CH_3$, $(RO)_3,PS$ where $R=CH_3$ and $R'=alkyl$, $MeP(S)Cl_2$, $(RO)_2(S)PSP(S)(OR)_2$, $P(S)(SH)$, $(RO)(R'S)P(O)SZn^-$, $SPH(OCH_3)_2$, and combinations thereof.

31. The lubricant produced by the process of claim 26 wherein the lubricant additive is formed by heating the metal fluoride and the pentavalent, mono- or di-thiophosphate together from about 20 minutes to about 24 hours.

32. A method for producing a lubricant comprising:
reacting ferric fluoride with ZDDP at a temperature range of about 60° C. to about 125° C. for a period of about 20 minutes to about 24 hours, wherein the ferric fluoride acts primarily as a reactant, and wherein said reacting produces a reaction mixture; and
adding at least a portion of said reaction mixture to a lubricant base, the reaction producing, in the mixture, at least one compound that comprises at least one phosphorus-fluorine bond.

* * * * *